(12) United States Patent
Van Der Linden et al.

(10) Patent No.: US 7,549,973 B2
(45) Date of Patent: Jun. 23, 2009

(54) DEVICE FOR THE SUPPLY OF A GAS

(75) Inventors: Jan Van Der Linden, Saltsjöbaden (SE); Mikael Persson, Stockholm (SE)

(73) Assignee: Cardia Innovation AB (SE)

( * ) Notice: Subject to any disclaimer, the term of this patent is extended or adjusted under 35 U.S.C. 154(b) by 226 days.

(21) Appl. No.: 10/507,467

(22) PCT Filed: Apr. 15, 2002

(86) PCT No.: PCT/SE02/00740

§ 371 (c)(1),
(2), (4) Date: Sep. 10, 2004

(87) PCT Pub. No.: WO03/086220

PCT Pub. Date: Oct. 23, 2003

(65) Prior Publication Data

US 2005/0119607 A1    Jun. 2, 2005

(51) Int. Cl.
*A61M 37/00*    (2006.01)
(52) U.S. Cl. ........................................ 604/23
(58) Field of Classification Search ............ 604/23–26, 604/289–290, 304–308; 602/42–43, 46
See application file for complete search history.

(56) References Cited

U.S. PATENT DOCUMENTS

| | | | | |
|---|---|---|---|---|
| 690,224 A | * | 12/1901 | Bagby | ........................ 431/158 |
| 2,637,106 A | * | 5/1953 | Otis | ............................ 433/91 |
| 3,520,300 A | * | 7/1970 | Flower, Jr. | .................. 604/269 |
| 3,672,372 A | * | 6/1972 | Heimlich | ..................... 604/544 |
| 3,853,332 A | | 12/1974 | Lynch | |
| 3,923,482 A | * | 12/1975 | Knab et al. | .................... 55/412 |
| 4,624,656 A | * | 11/1986 | Clark et al. | .................... 604/23 |
| 5,738,656 A | * | 4/1998 | Wagner | ....................... 604/119 |
| 6,994,685 B2 | * | 2/2006 | van der Linden | .............. 604/26 |

FOREIGN PATENT DOCUMENTS

| | | | | |
|---|---|---|---|---|
| GB | 2220357 A | * | 1/1990 | |
| WO | WO 7900546 | | 8/1979 | |
| WO | WO 99/13793 | * | 3/1990 | |
| WO | WO 99/13793 | * | 3/1999 | |
| WO | WO 99/29249 | | 6/1999 | |
| WO | WO 0145790 | | 6/2001 | |

* cited by examiner

*Primary Examiner*—Nicholas D Lucchesi
*Assistant Examiner*—Theodore J Stigell
(74) *Attorney, Agent, or Firm*—Greer, Burns & Crain, Ltd.

(57) ABSTRACT

A device for supply of a gas to a volume includes a supply conduit, which is connectable to a gas source and which includes an outlet end, and a porous body, which is provided at the outlet end. The device is arranged to permit the supply of the gas through the porous body. The device includes an attachment member which includes a surface and a channel extending through the surface. The porous body is attached to the surface and the outlet end is connected to the attachment member in order to permit the supply via the channel.

18 Claims, 2 Drawing Sheets

DEVICE FOR THE SUPPLY OF A GAS

THE BACKGROUND OF THE INVENTION AND PRIOR ART

The present invention refers to a device for the supply of a gas. Such a device is disclosed in the previous application of the applicant, WO01/45790.

During surgery, which is performed in an open manner, i.e. when an inner portion of the body is uncovered for the performance of the surgical operation, it can be important to prevent air from the surroundings to reach the open portion of the body in order to avoid infections, for instance. Such infections may be caused by microorganisms and bacteria, which are always present in the surrounding air and which fall down towards the open portion of the body. It is thus desirable to create a protecting atmosphere around the open portion in order to protect said inner portion from non-sterile air and also falling particles. In addition, different surgical operations may involve various requirements on the protecting atmosphere. In this connection it is referred to WO01/45790, which discloses the supply of a gas for the formation of such an atmosphere.

In order to create such a protecting atmosphere around, for instance, a temporary open, inner portion of a human being, it is important to avoid the formation of turbulence in the supplied gas volume, which should form the protecting atmosphere, since the turbulence may involve mixing of air from the surroundings in the gas volume. WO01/45790 proposes the use of a foam rubber body for the supply of a gas with a controlled laminar flow at an extremely low flow velocity from the surface of the porous foam rubber body.

SUMMARY OF THE INVENTION

The object of the present invention is to provide a device for the supply of a gas to an area. Especially, it is aimed at such a device for creating a protecting gas atmosphere in said area or in a cavity. Such an area may for instance adjoin an outwardly open, inner portion of the body of a human being or an animal.

This object is obtained by the device initially defined, which is characterised in that it includes an attachment member, which includes a surface and a channel extending through the surface, wherein the porous body is attached to said surface and wherein the outlet end is connected to the attachment member for permitting said supply via said channel.

Such a device is suitable for the supply of gas in several different contexts in the medical services or industry in order to create a clean protecting gas atmosphere. A plurality of different gases may be supplied by the device, for instance carbon dioxide, oxygen gas, air, nitrogen gas, etc.

By such an attachment member, a sufficiently large surface may be created for attaching the porous body in a secure manner. Furthermore, the porous body will be kept stretched during use so that unintentional total compression thereof is made significantly more difficult. However, it is also possible to manually compress the porous body by pressing it axially towards the surface of the attachment member and in such a way press out a liquid, for instance blood, from the porous body. A large quantity of liquid in the body may deteriorate its capability of providing a laminar gas flow. By such an attachment member, also the outflow direction or outflow directions of the gas supplied through the porous body will be guided, for instance to flow outwardly from the body forwardly and laterally. A rearward flow may for instance be prevented in an efficient manner. By such an attachment member, also less turbulence may be obtained in the volume to which the gas is supplied. The attachment member and the porous body may be manufactured with small dimensions and thus be provided very close to or in said area.

According to an embodiment of the invention, said surface of the attachment member covers substantially the whole porous body seen in a first direction extending from the attachment member through the body. In such a way, gas is efficiently prevented from flowing rearwardly from the porous body. However, the surface may also have a smaller extension and permit a certain rearward flow.

According to a further embodiment of the invention, the attachment member includes a sleeve, which extends outwardly away from the porous body and which is connected to the outlet end, wherein the channel extends through the sleeve. The sleeve may advantageously extend in a direction forming an angle to the first direction, wherein said angle is 0 to 90°. Either the supply conduit projects into the sleeve or the sleeve projects into the supply conduit.

According to a further embodiment of the invention, the attachment member and the porous body are substantially circular seen in the first direction. Such a shape is uniform and secures a uniform flow in all directions extending radially from the first direction. Furthermore, the porous body may have a substantially semi-spherical surface which faces away from the attachment member. In such a way also a uniform flow in all directions forwardly, i.e. with a component in the first direction, is ensured.

According to a further embodiment of the invention, the supply conduit includes at least a first conduit portion with a casing of a material, which has a large flexibility, and with a means for stiffening, which extends along the casing and has a lower flexibility than the casing. By means of such a construction, a large bendability of the supply conduit is obtained in such a way that it may be bent to any shape permitting the body to be positioned in a advantageous manner in said volume. Furthermore, the stiffening means permits the supply conduit to maintain the shape obtained during use of the device. Thus the stiffening means may be plastically deformable and may for instance include a metal wire. Furthermore, the stiffening means may advantageously extend substantially freely within the supply conduit and more precisely within the first conduit portion.

According to a further embodiment of the invention, the porous body is manufactured of a foam rubber-like material. Such a material has a low weight and is therefore easy to handle in sensible environments. Foam rubber materials are also inexpensive. Advantageously, the foam rubber-like material includes polyurethane foam with a very large quantity of adjacent, small open cells, which may function as supply nozzles for the gas. The porous body may also be manufactured of a permeable material including at least one of paper, felt, sinter metal and filter material. Furthermore, the porous body may include a homogenous body, for instance with regard to the porous material being substantially uniform with a substantially uniform cell size in the whole body. However, it is also possible to let the body have an inner larger cavity defining an inner surface of a wall, wherein the gas flows into the cavity through the porous wall of the body. The outer shape of the body may be homogenous in the sense that the surface is substantially uniform, as in the above-mentioned substantially semi-spherical shape or a spherical or more oblong shape.

According to a further embodiment of the invention, the device includes a filter, which is arranged on the supply conduit for filtering of said gas flowing through the supply conduit. By means of such filter, the gas to be supplied may be purified from particles and microorganisms.

According to a further embodiment of the invention, said gas includes a main component which is carbon dioxide. Carbon dioxide has a higher density than air and will therefore sink downwardly and form a gas cushion at or above said area. Carbon dioxide has several medical advantages, which appear from the previous application of the applicant, WO99/

29249. The gas may also be a mixture of one or several main components, such as carbon dioxide and/or oxygen, and different additional components, such as steam, disinfectants, sterilising substances, inclusive alcohol, solved medicaments, including anticoagulants, antibiotic, hormones, tissue factors etc.

According to a further embodiment of the invention, the porous body is arranged to supply said gas in a controlled flow in order to enable the formation of a gas cushion, which is intended to substantially fill a volume at said area and thus to prevent air from the surroundings to reach said area. Said area may advantageously adjoin an inner portion of the body of a human being or an animal, which portion is open outwardly towards the surroundings, wherein the porous body is arranged to be located at said outwardly open inner portion.

BRIEF DESCRIPTION OF THE DRAWINGS

The invention is now to be described more closely by means of different embodiments and with reference to the drawings attached.

DETAILED DESCRIPTION OF DIFFERENT EMBODIMENT OF THE INVENTION

Figure 1:
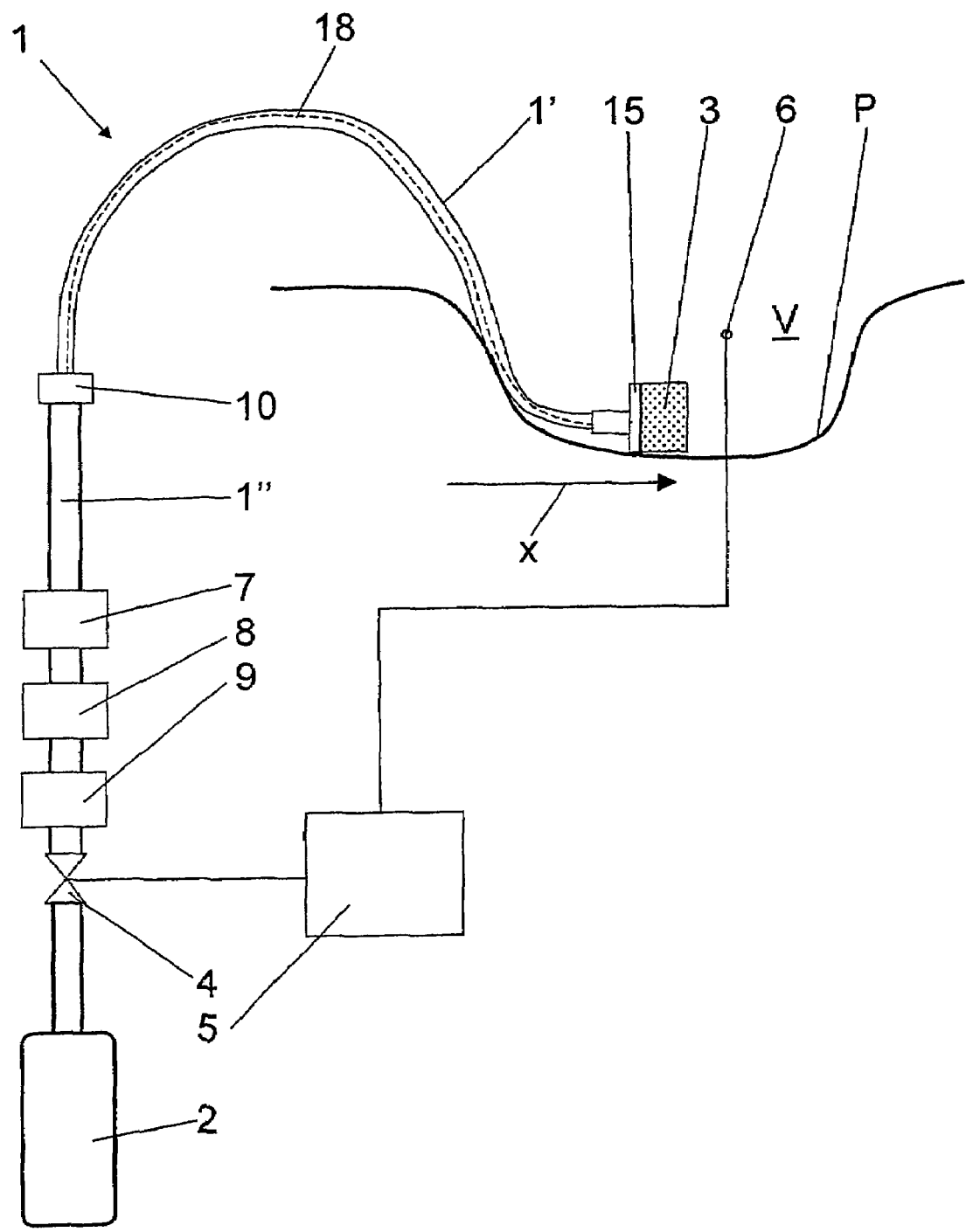
FIG. 1 discloses schematically a view of a device according to an embodiment of the invention.
Figure 2:
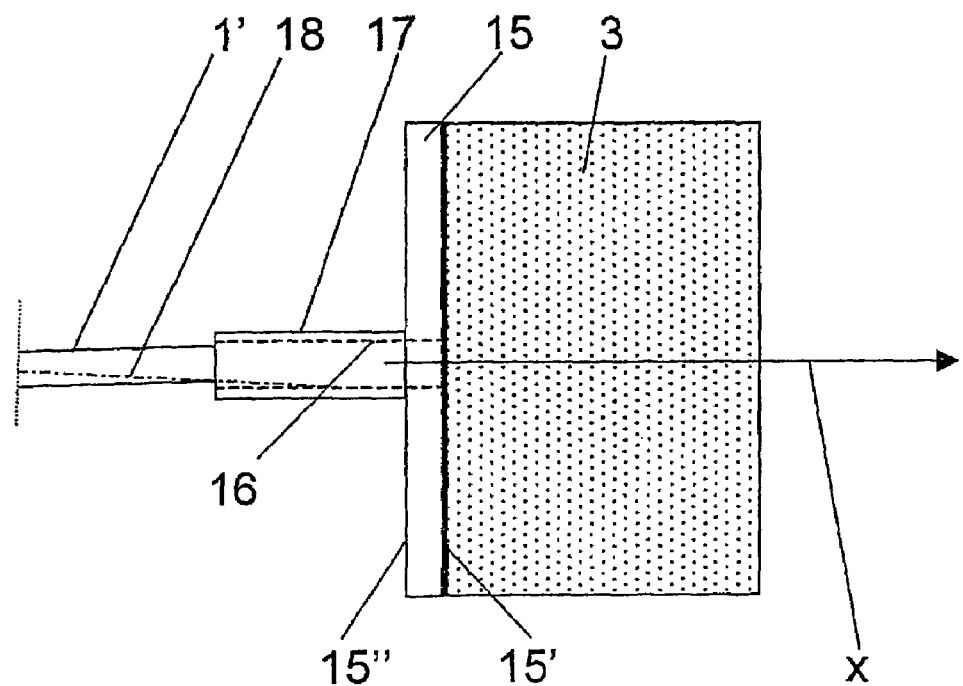
FIG. 2 discloses a view of a body of the device in FIG. 1.

FIGS. 1 and 2 disclose a device according to a first embodiment of the invention. The device disclosed is intended to create a protecting atmosphere in an area which here is exemplified by a concave volume V adjoining a temporary open, inner portion P of a human being in order to prevent air from the surroundings from reaching the volume V. It is to be noted that the area and thus the inner portion P also may be substantially plane or even slightly convex. Such an open portion P is formed during operations performed in an open manner, i.e. when an inner portion P of the body is uncovered for the performance of the surgical operation. In connection with for instance heart surgery, a substantial part of the interior of the thorax is uncovered so that this normally has direct contact with the surrounding atmosphere, i.e. with air. However, it is to be noted that the device according to the invention may be applied in many different contexts for the supply of gas to various volumes V. The device is designed in such a way that it permits a controlled gas supply substantially without turbulence, which has the advantage that if the supplied gas is heavier than air the gas may form a continuous gas cushion, which remains at the area.

The device includes a supply conduit 1 with an inlet end, which is connectable to a gas source 2, for instance in form of a conventional pressurised gas container. According to a preferred application of the invention, the gas source 2 contains a gas which consists substantially of pure carbon dioxide or has a main component consisting of carbon dioxide. The gas may also contain various additional components in form of gases, liquids or particles, for instance disinfectant gases. It is also possible to let the gas contain various medicaments, which may be supplied to a patient by means of the device via the open portion P. The supply conduit 1 also has an outlet end. Furthermore, the device includes a porous body 3, which is arranged at the outlet end. The gas is arranged to be supplied to the volume V through the supply conduit 1 and the porous body 3 in a controlled flow in order to enable the formation of a gas cushion, which is intended to substantially fill said volume V. Air, particles and micro-organisms from the surroundings are thus prevented from reaching the volume V.

The device may be connected to or include a control valve 4 by means of which the gas supply to the porous body 3 is controllable. In the example disclosed, the control valve 4 is controlled by means of a control unit 5 connected to the control valve 4. The control unit 5 may in its turn be connected to a gas sensor 6, which is arranged to sense the concentration of for instance the gas supplied or air in the volume V concerned. By means of such a sensing, the gas supplied to the volume V may be controlled in such a way that if an increased air concentration is detected, also the gas supply is increased, or if the air concentration in the volume V exceeds a predetermined level the gas supply is increased.

The device may also include a humidifying member 7, which is connected to the supply conduit 1 and which permits humidification of the gas to be supplied with water or steam. In such a way, drying of the tissue in the open portion P may be prevented. Furthermore, the device may include a cooling member and/or a heating member 8, which may be provided upstream and/or downstream the humidifying member 7 and which permits cooling of the gas to be supplied to a temperature which is somewhat lower than the temperature of the surrounding atmosphere. The cooling has the advantage that the gas thanks to its lower temperature is given a higher density and consequently becomes heavier. In such a way, the gas may more easily displace the surrounding air in the volume V concerned. Cooling of surfaces, for instance an operation wound, may be sped up, partly by the supply of the cooled gas with a homogenous laminar flow by means of the cooling member 8 and partly by the fact that the supplied gas or gas mixture is not humidified. Thus the evaporation from the surface is promoted more than normally, which leads to a cooling. In this manner, the temperature and the perfusion of blood of a tissue during a limited time may be significantly reduced.

A skin surface, a wound surface or a wound volume exposed to the surrounding air cools the patient not only locally at the surface but also the whole body of the patient. The supply of a heated gas by means of a heating member 8 to the exposed surface or volume will have an isolating or heating effect to the surface or the volume against such a cooling. The cooling of an exposed surface is caused for instance of the evaporation of liquid from the surface. Since the gas is saturated with moisture by means of the humidifying member 7 the surface is isolated from the cooling evaporation since no liquid absorption from the surface to the supplied gas may take place. Since the evaporation and the cooling of a body surface or an operation wound in this way is prevented, the perfusion of blood will be higher than if the evaporation and cooling of the portions mentioned above take place. The device may include a supply member 9 for the supply of the additional components mentioned above. Furthermore, the device includes a filter 10, which is arranged on the supply conduit 1 for filtering of said gas flowing through the supply conduit 1.

The porous body 3 may be manufactured of a foam rubber-like material having a large number of open cells, which distributes the gas flow from the supply conduit 1 homogeneously in the porous body 3 so that the gas flow is distributed uniformly over its surface. This leads to low outflow velocities despite a very high inflow velocity from the supply conduit 1. The cells, which lie very close to each other, thus function as multiple supply nozzles, which permit the gas leaving the porous body to form a substantially laminar, continuous slow gas flow enabling the formation of the gas cushion. The porous body 3 is in the embodiment disclosed totally manufactured of said foam rubber-like material and thus forms a homogenous foam-rubber body 3. Such a suitable material is for instance polyurethane foam with open cells and with a density of between for instance 20 and 40 kg/M$^3$.

The porous body 3 may also include or consist of other materials than foam rubber materials, for instance porous sintered plastics and other porous permeable materials, for instance of paper, felt, sinter metal and/or filter material.

The device includes an attachment member 15, which is provided adjacent to the porous body 3. The attachment member 15 is in the embodiment disclosed shaped as a substantially plane plate with a first surface 15' and a second opposite surface 15", see FIG. 2. In the embodiment disclosed, the surfaces 15', 15" are substantially plane. It is to be noted, however, that the first surface 15' may have another shape, for instance a concave or convex shape. The first surface 15' may for instance be conical and thus permit at least a certain rearward flow. The shape of the first surface 15' may thus be utilised for guiding the outflow direction(s) of the gas. However, it is to be noted that the first surface 15' is to be at least partly directed forwardly in a forward direction x. The first surface 15' thus faces away from the second surface 15". The second surface 15" may have a substantially arbitrary shape. The attachment member 15 is manufactured in any suitable material, for instance PVC plastics. The attachment member 15 may also be manufactured of any other material of plastics, rubber or metal. The attachment member 15 includes a channel 16, which extends through said surfaces 15', 15" and through which the gas. is conveyed in the first forward direction x into the porous body 3. The porous body 3 is attached to the first surface 15' in a suitable manner, for instance through melting, gluing or vulcanisation. Furthermore, the attachment member 15 includes a sleeve 17, which extends outwardly from the second surface 15" and thus away from the porous body 3. The sleeve 17 may, as in the embodiment disclosed, extend substantially in parallel with the first forward direction x but also in any other direction. The channel 16 extends thus through the tubular sleeve 17, which is connected to the first conduit portion 1'.

The supply conduit I includes a first conduit portion 1', which in the embodiment disclosed extends between the filter 10 and the attachment member 15, and a second conduit portion 1", which extends between the gas source 2 and the filter 10. It is to be noted that the filter 10 may be provided in another position in relation to the arbitrary members 7, 8 and 9. For instance, the filter 10 may be provided substantially immediately downstream the gas source 2. The first conduit portion 1' includes and is defined by a casing in the form of a thin flexible hose. The casing is thus manufactured of a material with a large flexibility, for instance a rubber material or plastic material such as silicon and PVC. Furthermore, the supply conduit 1 includes a means for stiffening in the form of a stiffening member 18, which extends along the first conduit portion 1 and which has a lower flexibility than the casing. The stiffening member 18 may be attached to one or both ends of the conduit portions 1', for instance to the inner wall of the sleeve 17 and in the transition between the filter 10 and the first conduit portion 1'. The stiffening member 18 may also be freely provided in the conduit portion 1' or be attached along its inner or outer side. A further possibility is that the stiffening member 18 is moulded in the wall of the conduit portion 1'. The stiffening member 18 is plastically deformable without any substantial elasticity. The stiffening member 18 thus has a capability of remaining in the shape to which it is bent. Advantageously, the stiffening member 18 may include or be manufactured of a metal wire, for instance of stainless steel. In the embodiments disclosed, the stiffening member 18 extends within the first conduit portion 1'. The stiffening means may also be obtained by designing the casing proper, for instance by a folding of the casing.

The second conduit portion 1" may be formed of any thicker and stiffer hose or rigid pipe. The different components, the valve 4, the supply member 9, the cooling member 8, the humidifying member 7 and the filter 10 are in the embodiments disclosed arranged on the second conduit portion 1".

The outlet end of the supply conduit 1, which thus is included by the first conduit portion 1', is connected to the attachment member 15, in such a way that the gas supply may take place via the channel 16. In the embodiments disclosed the first conduit portion 1' projects into the sleeve 17 and is connected to the inner wall of the channel 16, for instance by melting, gluing or vulcanisation. However, it is to be noted that it is also possible to connect the sleeve 17 to the outlet end of the supply conduit 1 by letting the sleeve 17 project into the first conduit portion 1', wherein the first conduit portion 1' may be connected to the outer wall of the sleeve 17 by any of the above-mentioned methods melting, gluing or vulcanisation or by shrinking the first conduit 1' onto the sleeve 17.

Figure 3:
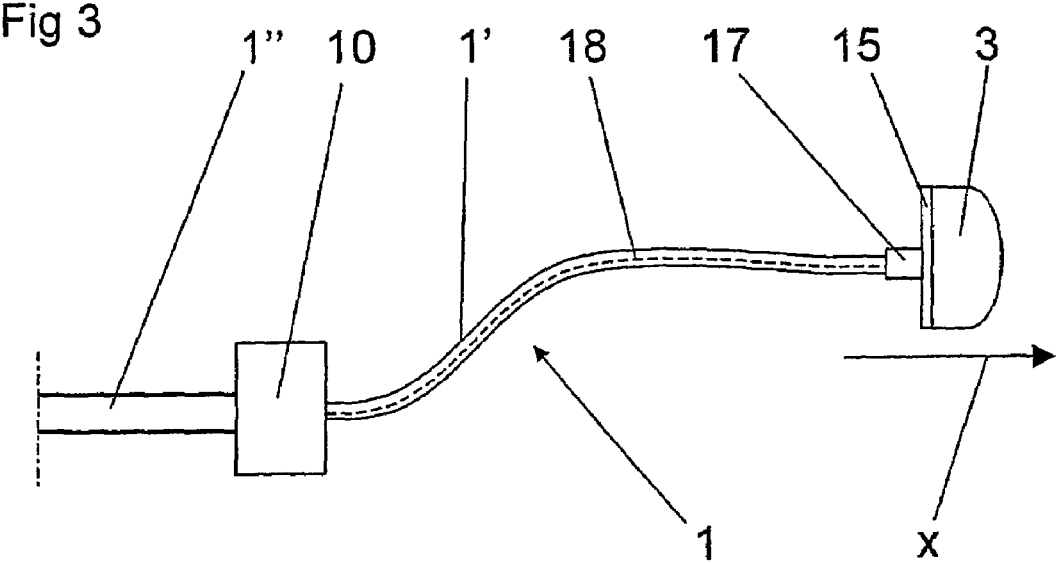
FIG. 3 discloses a part of the device according to a second embodiment of the invention.

Preferably, but not necessarily, said surfaces 15', 15" of the attachment member 15 cover substantially the whole porous body 3 seen in a first direction x, which extends through the attachment member and the body, and more precisely through the channel. In the embodiments disclosed, the attachment member 15 and the porous body 3 are substantially circular seen in the first direction x. This shape is advantageous since it permits a uniform flow in all radial directions. However, it is possible to let the attachment member and the porous body 3 have other cross-sectional shapes, for instance oval, rectangular or square shapes. In the embodiments disclosed in FIG. 1, the porous body 3 has a substantially cylindrical shape extending from the first surface of the attachment member 15 in the first direction x. In the embodiment disclosed in FIG. 3, the porous body 3 has a substantially semi-spherical shape with an outer semi-spherical surface facing away from the first surface 15' of the attachment member 15.

The invention is not limited to the embodiments disclosed but may be varied and modified within the scope of the following claims. For instance, the porous body 3 may advantageously be heparinised either by the measure a) that it is primarily during manufacturing coated with a heparinised surface, so-called heparin-coating b) that it just before use is saturated with active heparin, c) that the gas used contains heparin and/or d) that blood or liquids, which possibly will come into contact with the porous body 3, already are heparinised and thus blood or liquids will not to the same extent be able to block the open cells of the porous body 3.

In a further embodiment of the invention, the porous body 3 is arranged not only to fill a volume with the gas supplied (such as a wound cavity or an open container) but in such a way that the gas will cover a surface lacking any cavity in order to a) prevent the falling down of particles including micro-organisms to the surface, b) prevent other gases, for instance air, from reaching the surface and/or c) coat the surface with or exposing the surface to one or several gaseous additional components such as steam, disinfectants, sterilising substances including alcohol, and/or dissolved medicaments, including anticoagulants, antibiotic, hormones, tissue factors, etc.

In a further embodiment of the invention, the porous body 3 is arranged to supply gases for inhalation, for instance oxygen gas, in front of the nose and/or the mouth, or in the nose and/or the mouth, wherein for instance oxygen gas or air form said main component. The porous body 3 may be separate or combined with other inhalation aiding means, for instance an oxygen mask. Therethrough an even more efficient supply of inhalation gas with its possible additives may be enabled. Also in this case a thin supplying hose with a stiffening means 18 for fixing the position and shape of the hose is advantageous. A separate porous body may for instance be attached by means of tape onto the patient or be arranged at any fixed holding structure, for instance of a microphone headset type. By such a supply system for oxygen gas one may in a sufficient manner avoid contact irritation at the nose and mouth which are sensible to pressure and/or heat and/or moisture. Furthermore, an efficient oxygen supply is obtained. A further advantage is that one may avoid the use of a nose catheter or a mask in front of the mouth and the nose, which make the communication with the patient more difficult.

In a further embodiment of the invention, the device consists of more than one porous body 3, which are arranged in parallel or series to the supplying supply conduit or supply conduits. The invention may thus include one or several advantageously thin supplying hoses, and one or several porous bodies 3.

The invention enables local protection above a surface or a volume against fire or chemical attacks, for instance oxidation from other surrounding gases such as air. If the gas supplied is for instance carbon dioxide, protection against these two types of attacks can be obtained. Because thereof otherwise flammable gases, additives, such as alcohol that is an disinfectant, are transported to a surface or a volume such as an operation wound since the main component of the supplied carrier gas is the fire protecting and fire extinguishing gas carbon dioxide.

The invention may as has been mentioned above also be applied within other fields.

The invention may also be applied within industry in order to create a clean gas atmosphere locally at a surface or in a cavity, for instance during mounting, soldering, packaging within the food industry and electronic/computer industry. In this case different types of gases may be used. In certain cases, inert gases of the type nitrogen gas may be advantageous.

The invention claimed is:

1. A system for the supply of a gas to an area, comprising:
   a gas source
   a supply conduit, which is connected to said gas source and which includes an outlet end;
   a porous body, which is manufactured of a foam rubber-like material and is provided at said outlet end, wherein the device is arranged to transmit said supply of gas through said foam rubber-like material of the porous body to create a protective gas atmosphere in the area;
   a filter arranged on the supply conduit for filtering said supply of gas flowing through the supply conduit; and
   an attachment member shaped as a substantially planar plate including a first surface, a second surface, a sleeve extending outwardly away from the porous body and being connected to the outlet end, and a continuous channel extending through the sleeve, said second surface, and the first surface, respectively;
   wherein the porous body is attached to said first surface and wherein the outlet end is connected to the attachment member for transmitting said supply in a direction through said outlet end, said channel and said porous body, respectively, for creating said protective gas atmosphere.

2. A device according to claim 1, wherein said first surface of the attachment member covers substantially the whole porous body seen in a first direction extending from the attachment member through the body.

3. A device according to claim 2, wherein the attachment member and the porous body are substantially circular seen in the first direction.

4. A device according to claim 3, wherein the porous body has a substantially semispherical surface which faces away from the attachment member.

5. A device according to claim 1, wherein the sleeve extends in a direction forming an angle to the first direction x, wherein said angle is 0 to 90°.

6. A device according to claim 1, wherein the supply conduit projects into the sleeve, or that the sleeve projects into the supply conduit.

7. A device according to claim 1, wherein the supply conduit includes at least a first conduit portion with a casing of a material, which has a large flexibility, and with a means for stiffening, which extends along the casing and has a lower flexibility than the casing.

8. A device according to claim 7, wherein the stiffening means is plastically deformable.

9. A device according to claim 7, wherein the stiffening means includes a metal wire.

10. A device according to claim 7, wherein the stiffening means extends substantially freely within the first conduit portion of the supply conduit.

11. A device according to claim 1, wherein the foam rubber-like material includes polyurethane foam with open cells.

12. A device according to claim 1, wherein the porous body includes a homogenous body.

13. A device according to claim 1, wherein said gas includes a main component which is carbon dioxide.

14. A device according to claim 1, wherein the porous body is arranged to supply said gas in a control flow in order to enable formation of a gas cushion, which is intended to substantially fill a volume at said area and thus prevents air from the surroundings to reach said area.

15. A device according to claim 1, wherein said area adjoins an inner portion of the body of a human being or an animal, which portion is open outwardly towards the surroundings, wherein the porous body is arranged to be located at said outwardly open inner portion.

16. The device of claim 1 wherein said filter is configured to purify said gas from particles and microorganisms.

17. A system for the supply of a gas to an area, comprising:
    a gas source;
    a supply conduit connected to said gas source, including an outlet end;
    a filter arranged on said supply conduit for filtering said supply of gas flowing through said supply conduit;
    an attachment member shaped as a substantially planar plate connected to said outlet end; said attachment member including a first surface, a second surface located opposite said first surface, a sleeve connected to the outlet end, and a centrally located continuous channel configured for receiving said supply conduit and extending through said sleeve, said second surface, and said first surface, respectively; and
    a porous body, which is manufactured of a foam rubber-like material, provided at said outlet end and having a proximal end attached to said first surface and a distal end free of attachment, the porous body being in direct fluid communication with said supply conduit and arranged to transmit the supply of gas in a direction through the outlet end, the channel and the porous body, respectively, for creating a protective gas atmosphere in the area, said sleeve extending outwardly away from the porous body.

18. A device according to claim 17, wherein said porous body is manufactured of a permeable material including at least one of paper, felt, sinter metal and filter material.

* * * * *